United States Patent
Cohen et al.

(10) Patent No.: US 7,006,865 B1
(45) Date of Patent: Feb. 28, 2006

(54) AUTOMATIC DEFIBRILLATOR MODULE FOR INTEGRATION WITH STANDARD PATIENT MONITORING EQUIPMENT

(75) Inventors: Raymond W. Cohen, Orange, CA (US); Dongping Lin, Irvine, CA (US); Mike Norton, Riverside, CA (US); Patrick Bradley, Corona del Mar, CA (US); Gary Mezack, Norco, CA (US); David Clark, Irvine, CA (US)

(73) Assignee: Cardiac Science Inc., Irvine, CA (US)

( * ) Notice: Subject to any disclaimer, the term of this patent is extended or adjusted under 35 U.S.C. 154(b) by 0 days.

(21) Appl. No.: 09/523,912

(22) Filed: Mar. 9, 2000

(51) Int. Cl.
*A61N 1/40* (2006.01)

(52) U.S. Cl. ........................................................... 607/5

(58) Field of Classification Search ................ 607/4–8; 600/518, 508
See application file for complete search history.

(56) References Cited

U.S. PATENT DOCUMENTS

| | | | | |
|---|---|---|---|---|
| 4,096,856 A | * | 6/1978 | Smith et al. | 607/5 |
| 4,097,113 A | * | 6/1978 | McKelvy | 439/377 |
| 4,295,474 A | | 10/1981 | Fischell | 428/697 |
| 4,590,943 A | * | 5/1986 | Paull et al. | 607/5 |
| 4,635,639 A | * | 1/1987 | Hakala et al. | 607/4 |
| 4,974,600 A | * | 12/1990 | Reyes | 600/509 |
| 5,285,792 A | * | 2/1994 | Sjoquist et al. | 600/510 |
| 5,342,403 A | * | 8/1994 | Powers et al. | 607/5 |
| 5,391,187 A | * | 2/1995 | Freeman | 607/5 |
| 5,549,659 A | * | 8/1996 | Johansen et al. | 607/60 |
| 5,605,150 A | * | 2/1997 | Radons et al. | 600/300 |
| 5,716,380 A | * | 2/1998 | Yerkovich et al. | 607/5 |
| 5,782,878 A | * | 7/1998 | Morgan et al. | 607/5 |
| 6,289,243 B1 | * | 9/2001 | Lin et al. | 607/5 |
| 6,321,113 B1 | * | 11/2001 | Parker et al. | 607/5 |
| 6,405,083 B1 | * | 6/2002 | Rockwell et al. | 607/5 |

* cited by examiner

*Primary Examiner*—Mark Bockelman
(74) *Attorney, Agent, or Firm*—Gottlieb, Rackman & Reisman, P.C.

(57) ABSTRACT

A defibrillator module is described which includes a cardiac sensor, a pulse generator and a controller that generates commands responsive to intrinsic cardiac signals for the operation of said pulse generator. The defibrillator module synergistic and arranged so that it can be coupled to a generic patient monitor so that the two can share certain functions. For example, operational parameters and other signals indicative of the operation of the defibrillator module can be shown to the clinician by the patient monitor. Data between the defibrillator module and the patient monitor is exchanged using either a standard or a customized protocol.

21 Claims, 17 Drawing Sheets

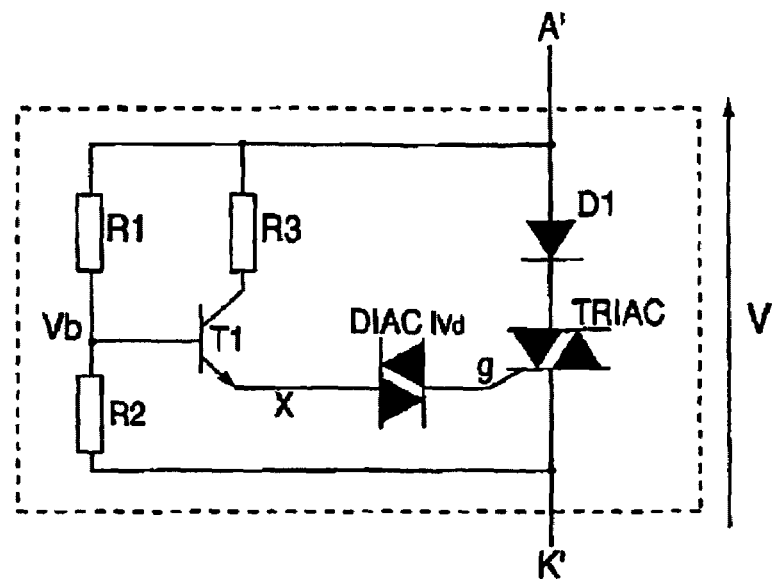
FIG. 4E
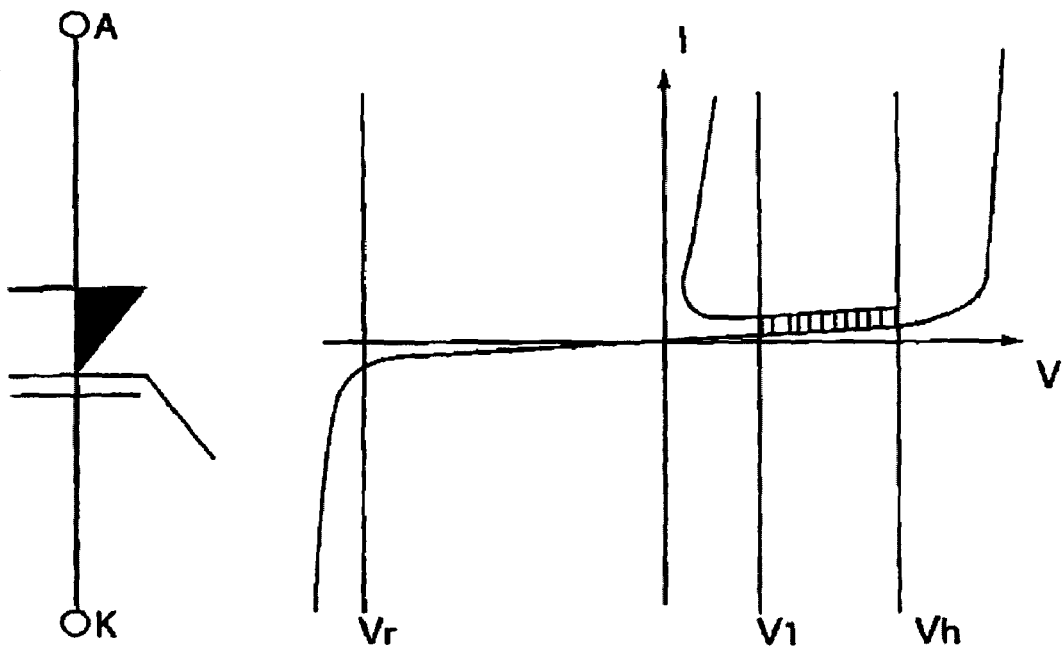
FIG. 4G
FIG. 4H

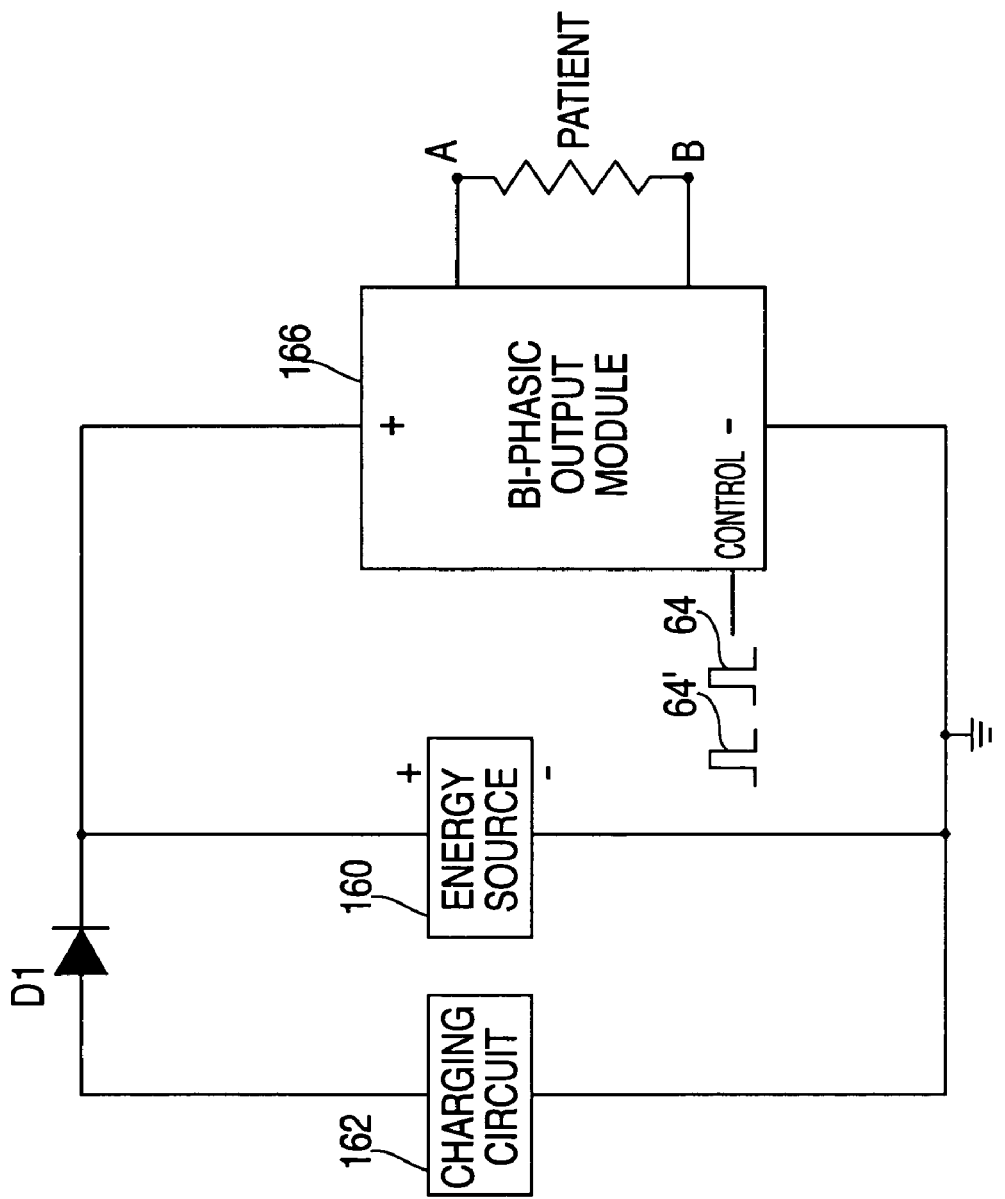

AUTOMATIC DEFIBRILLATOR MODULE FOR INTEGRATION WITH STANDARD PATIENT MONITORING EQUIPMENT

BACKGROUND OF THE INVENTION

A. Field of Invention

This invention pertains to an external defibrillator module arranged and constructed to provide anti-tachyarrhythmia therapy to a patient. In particular, an automatic external defibrillator module is described which has several operational modes including a fully automatic mode in which shocks are delivered without any manual intervention, an advisory mode, a manual mode, and a pacer mode. Moreover, the invention pertains to a defibrillator module which is arranged and constructed for integration with patient monitoring equipment for sharing certain functions and information using a standard or customized protocol.

B. Description of the Prior Art

Defibrillators are devices which apply electric therapy to cardiac patients having an abnormally high heart rhythm or fibrillation. Two kinds of defibrillators are presently available: internal defibrillators which are implanted subcutaneously in a patient together with leads extending through the veins into the cardiac chambers, and external defibrillators which are attached (usually temporarily) to the patient. External defibrillators are used in most instances in case of an emergency, for example, when a patient has either suffered cardiac arrest or when a cardiac arrest is imminent. Typically, therefore external defibrillators are manual devices which must be triggered by a physician or other trained personnel. Internal or implantable defibrillators (and cardioverters) are implanted as a permanent solution for patients having specific well-defined cardiac deficiencies which cannot be treated successfully by other means. They generally operate in an automatic mode.

Commonly-owned U.S. Pat. No. 5,474,574 discloses an external defibrillator. Commonly-owned U.S. Pat. Nos. 4,576,170 and 5,474,574, incorporated herein by reference discloses external defibrillators.

Several patient monitoring systems are presently available in modular form which allow a clinician or other health professional to monitor and display various physiological parameters of a patient. Typically these units include several subassembly modules which cooperate to acquire data from the patient, to store the data electronically and to display information about a patient's physiological status. The systems may also be adapted to generate audible and/or visual alarms when certain criteria are met. Some systems may also be integrated into a communications network covering, for example, a part or even a whole hospital and on which data is exchanged for various purposes. Monitoring systems of this kind are available from GE Marquette Medical Systems of Milwaukee, Wis.; Agilent Technologies of Andover, Mass.; Spacelabs Medical of Redmond, Wash., and many other companies. However, typically these systems are passive in that their main purpose is to monitor, collect information and generate alarms. These systems cannot provide therapy.

OBJECTIVES AND SUMMARY OF THE INVENTION

An objective of the present invention is to provide an automatic defibrillator module which is capable of detecting a current cardiac condition of a patient and of providing appropriate therapy to the patient, when needed.

A further objective is to provide an automatic defibrillator module which can be interfaced with a existing or future patient monitoring systems in a manner which allows the system and the module to share information and other common functions.

Yet another objective is to provide an external defibrillator module with several modes of operation, including an automatic mode in which shocks are applied on demand in accordance with preprogrammed shock parameters and without any prompting from an attendant, an advisory mode in which an attendant is alerted to a shockable rhythm however the application of shocks must be initiated by the attendant, a manual mode in which the attendant determines how and when shocks should be applied and the preprogrammed shock parameters are ignored, and a pacer mode for pacing certain cardiac events.

Other objectives and advantages of the invention will become apparent from the following description of the invention.

Briefly, a composite monitoring system constructed in accordance with this invention comprises a patient monitor including a sensor arranged to sense a physiological characteristic of a patient and a signal processor coupled to said sensor and adapted to process the signal from said sensor and an output member; and a defibrillator module adapted to be selectively coupled to said patient monitor, said defibrillator module including a pulse generator responsive to commands to generate therapeutic pulses for the patient, and a data generator arranged to generate indication signals indicative of an operation of said defibrillator module; wherein said patient monitor and said defibrillator module cooperating when coupled to transfer said indication signal to said output member whereby said output member generates output signals corresponding to one of said patient characteristic and said indication signals. The patient monitor may include a display that can be used to show signals or data associated with either the physiological characteristics being monitored or information pertaining to the operation of the defibrillator module. The patient monitor could also include audible and visual alarms, a printer, and a connection to a network through which data could be sent to a remote location. All these components could be shared between the patient monitor and the defibrillator module. Data between the defibrillator module and the patient monitor is exchanged using either a protocol standardized for the monitor or by using a customized protocol.

BRIEF DESCRIPTION OF THE FIGURES

FIG. 4e is a circuit diagram of a breakover USD;

FIGS. 4f, 4g and 4h are, respectively, a circuit diagram, circuit symbol and I=V characteristics of a breakunder USD;

FIG. 11 illustrates a pulse generator with the output circuit being implemented as a single encapsulated integrated circuit component;

FIG. 12b is an example of the waveform that can be produced by the embodiment of FIG. 12a.

DETAILED DESCRIPTION OF THE INVENTION

Figure 1:
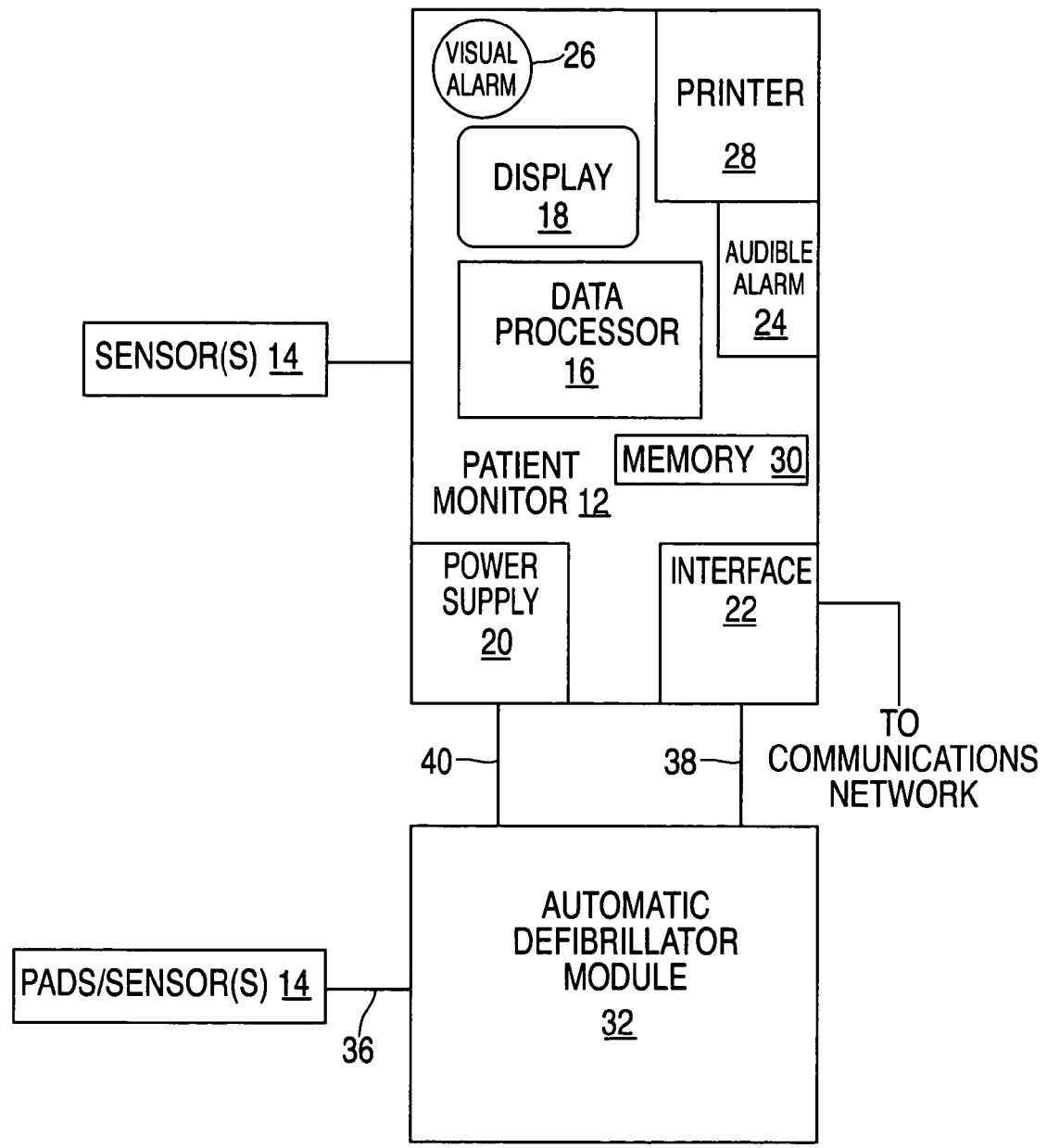
FIG. 1 shows a block diagram of a combined patient monitor and automatic defibrillator system.

Referring now to FIG. 1, a combined system 10 constructed in accordance with this invention includes a generic patient monitor 12 which is connected to one or more sensors 14 extending to the patient (not shown). The sensors 14 are used to obtain one or more physiological indicia from the patient, such as temperature, pressure, heart rate, respiration function, and so on. The monitor 12 includes a data processor 16, a display 18, a power supply 20, and data interface 22, which may for example be a standard serial or parallel port or any other data interface that may be used to exchange information with other components and/or a communications network (not shown). The monitor 12 may also include an audible alarm 24, a visual alarm 26 and a printer 28.

The data processor 16 in monitor 12 collects information from the patient through the sensors, processes this information and based on its programming, generates reports on the status of the patient. This status may be shown on display 18, and selectively a hard copy of the reports may be provided by printer 28. The status information may also be transmitted to remote locations via the interface 22 and the communications network. The monitor 12 may also include a memory 30 for logging the information regarding the status of the patient. The data processor 16 may also be adapted to determine if certain of the physiological parameters exceed certain preselected ranges or threshold values, these ranges or threshold values being selected to correspond to indicate abnormal or dangerous conditions for the patient. When such an event is detected, the data processor can activate the audible and/or the visual alarms 24, 26 to indicate that a danger condition has been detected.

As seen in FIG. 1, associated with monitor 12 there is provided an automatic defibrillator module (ADM) 32. The ADM is connected to its own set of sensors or defibrillator pads 34 via a cable 36. The purpose of providing the ADM 32 as a module rather than a stand-alone unit is so that it can share some of the functions and components of the monitor 12. For this purpose, the ADM 32 is connected to monitor 12 via a data cable 38 which acts as an output member and interfaces the ADM 32 with the monitor 12 as described in more detail below. Power to the ADM 32 can be provided by the power supply via a cable 40, or alternatively, the cable 40 may be connected to a standard line voltage outlet (not shown).

Figure 2:
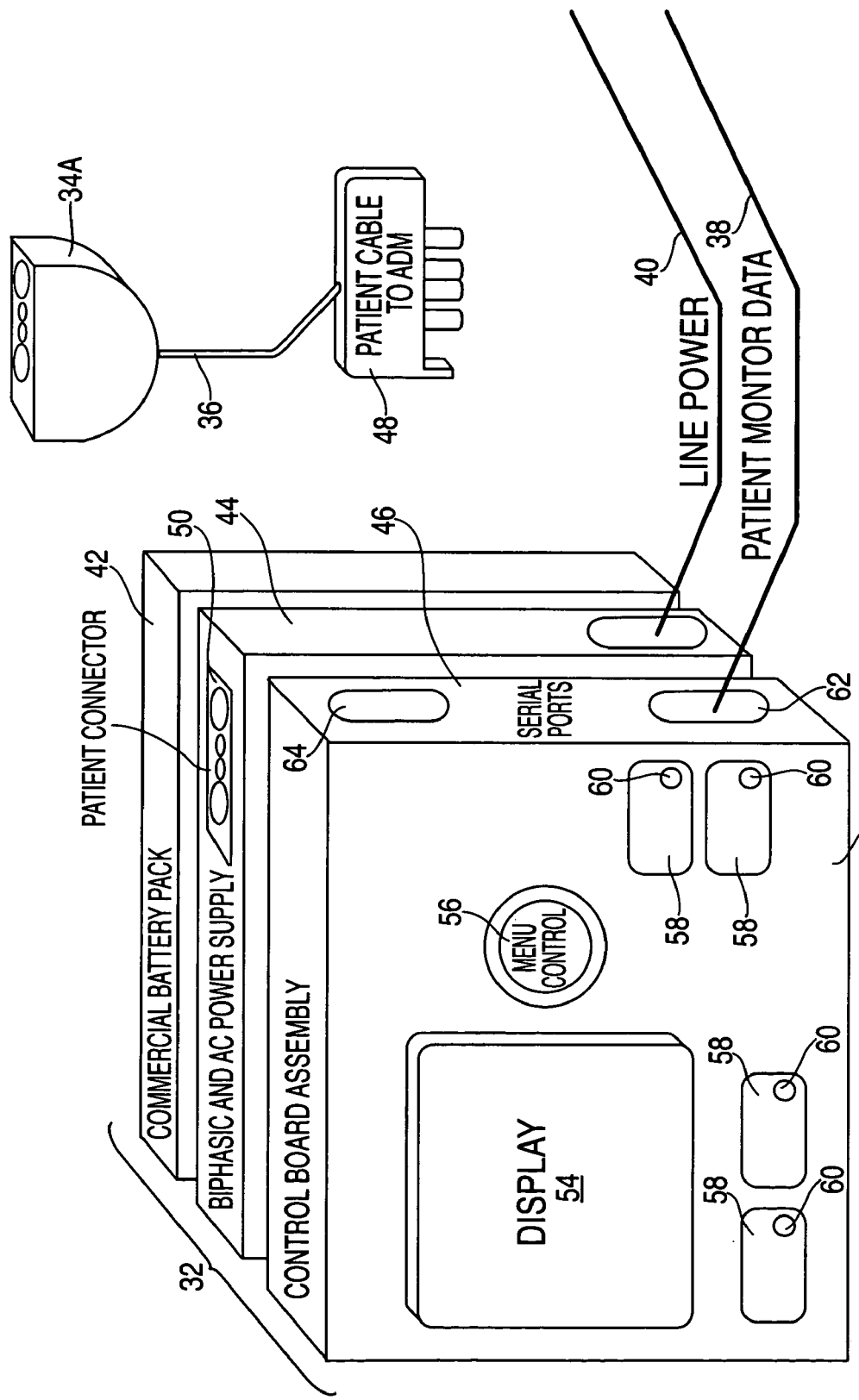
FIG. 2 shows a somewhat schematic isometric view of the automatic defibrillator module for the system of FIG. 1.

Referring now to FIG. 2, the ADM 32, in this configuration, consists of three assemblies: a battery pack 42, an assembly 44 including an AC power supply and biphasic pulse generator and a control board 46. The battery pack 42 consists of one or more batteries, which may be re-chargable by using energy from the AC power supply. The AC power supply is connected by cable 40 to monitor 12 or other line voltage source. The battery pack is used to provide high energy to the biphasic pulse generator of assembly 44. This energy is used as backup power source in the event of a AC power failure. The defibrillation pulses are transmitted by the cable 36 to the patient. For this purpose, the assembly 44 the cable 36 is provided with a connector 48 which mates with a connector 50 on the assembly 44.

The control assembly 46 contains the components required to control the operation of the ADM 32. As seen in FIG. 2, the assembly 46 includes a front face 52 formed with a display 54. Also provided on face 52 are a control knob 56 and a plurality of panel switches 58. Built into each of the switches 58 is an indication light 60. These lights are optional and may be omitted.

The control assembly 46 is further provided with two serial ports 62, 64. Serial port 62 is connected via cable 38 to monitor 12. The other port 64 may be used to connect the ADM 32 to other components.

The overall functionality of each component is more important than the number and the functional partition of assemblies. Another implementation may comprise more or less assemblies.

Figure 3:
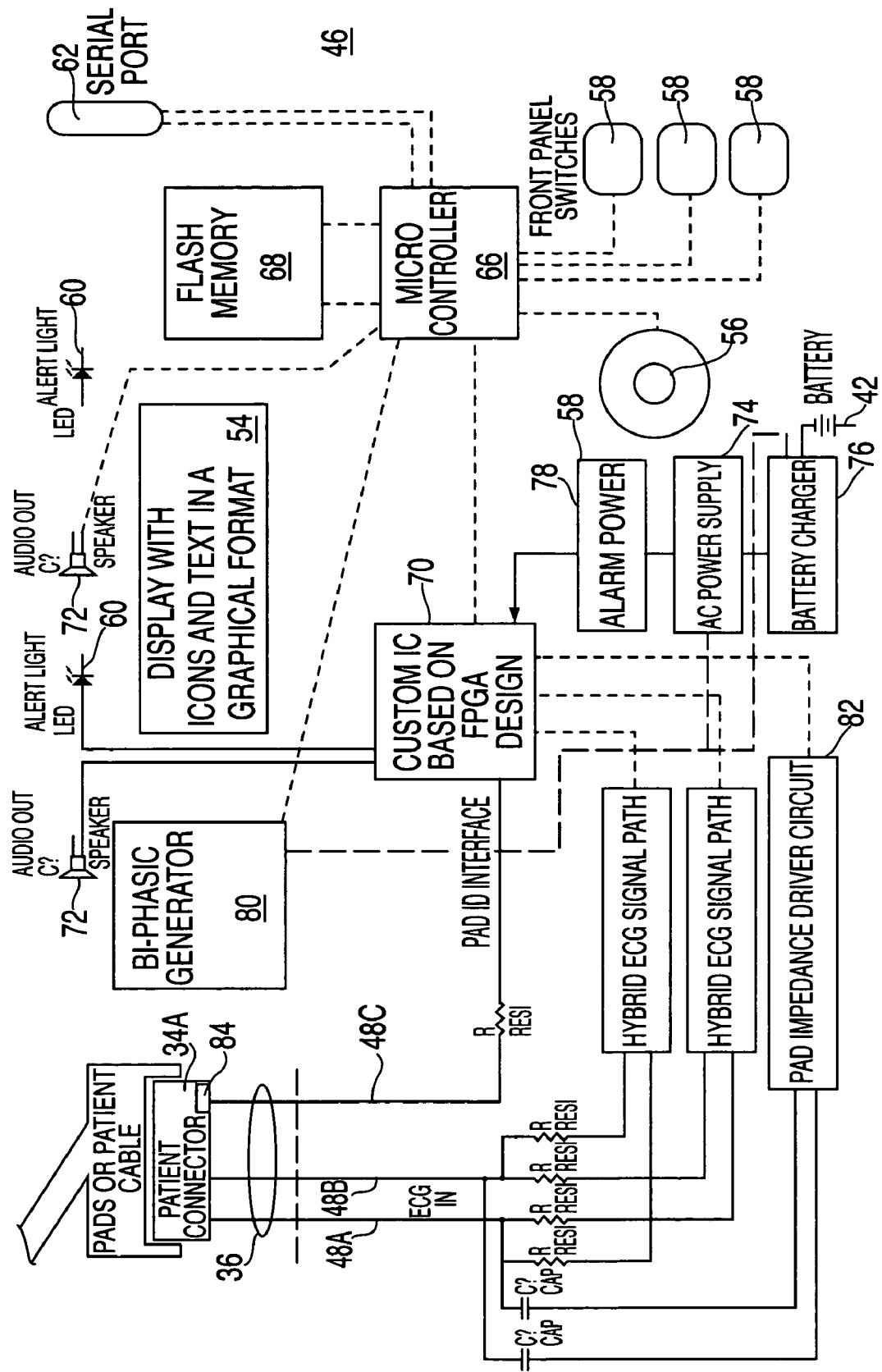
FIG. 3 shows a block diagram for the control assembly of the automatic defibrillator module incorporated into the system of FIG. 1.

FIG. 3 shows a block diagram of the ADM 32. The control assembly 46 includes a microprocessor or controller 66, a flash memory 68 and a custom control IC 70 which may be made using, for example, an FPGA design. The microprocessor 66 is connected to the serial port 62, switches 58, indicator lights 60 and the flash memory 68 and the custom IC 70 so that it can control the operation of the ADM 32. The flash memory 68 is used to store various operational parameters of the ADM 32 which can be either preset or selected by a clinician. These parameters can be set through the menu control knob 58 in conjunction with the switches 60 or via the patient monitor.

The lights 60 are activated either by the microprocessor 66 or by the custom IC 70. As discussed above, the ADM 32 is capable of generating audible as well as visual indication signals. The audible signals can be transmitted to the monitor 12 and/or to external speakers 72 (not shown in FIGS. 1 and 2). These audible signals can be generated by the microprocessor 66 and/or the custom IC 70.

Component 50 includes a power supply 74, a battery charger 76, an alarm power unit 78 and a biphasic pulse generator 80 (all shown in FIG. 3). The alarm power unit 78 provides the power required to drive the speakers 72 (if present). The battery charger 76 is used to charge the battery pack 42.

The biphasic pulse generator 80 receives dc power either from the power supply 74 or from the battery pack 42. The pulse generator 80 generates biphasic pulses in accordance with commands from the microprocessor 66.

A somewhat preferred implementation for the biphasic pulse generator 80 is now described, it being understood that this implementation does not constitute a part of the subject invention, and that other implementations may be used as well.

Figure 4A:
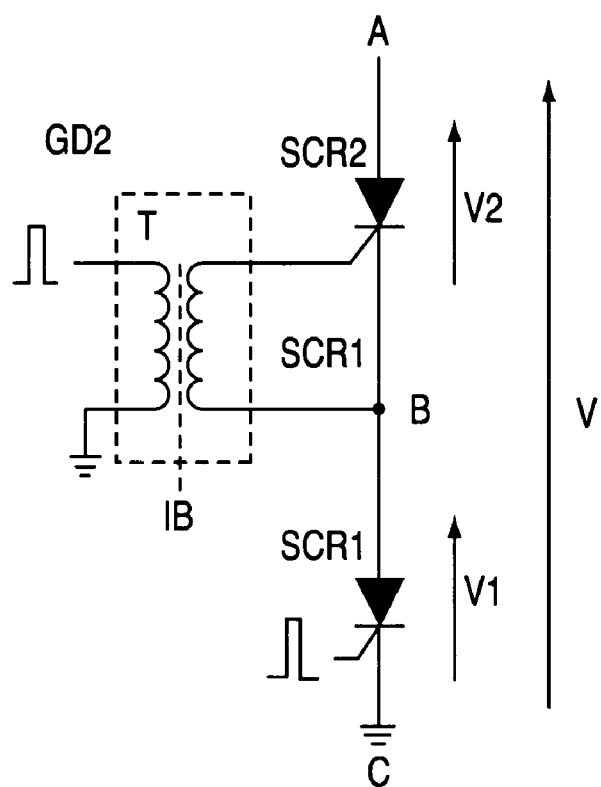
FIG. 4a shows a circuit illustrating the "totem-poling" of two SCRs so that the combination of the two devices can withstand a higher voltage than a single device.
Figure 4D:
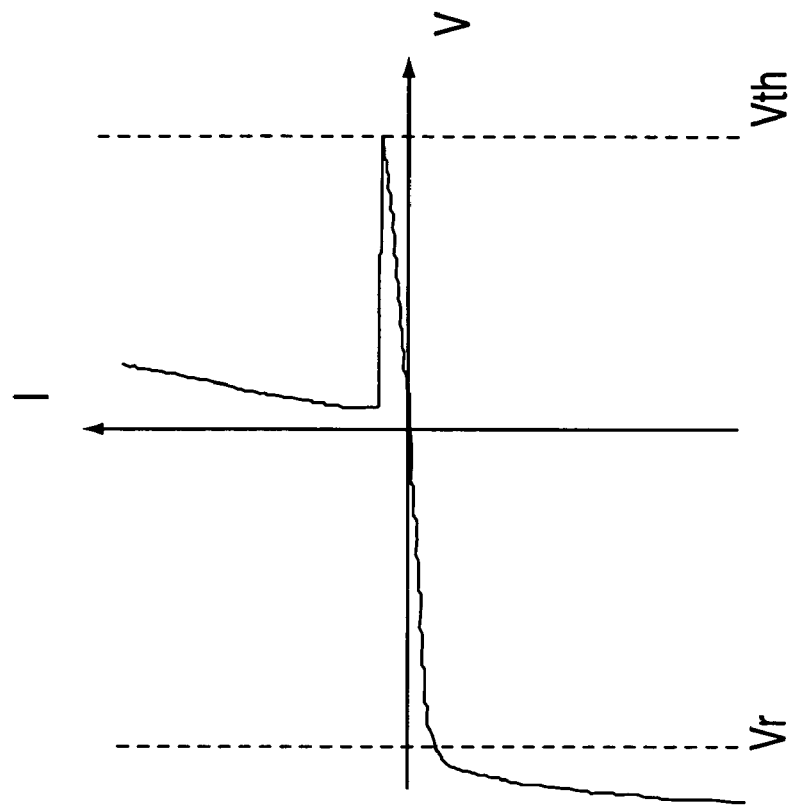
FIGS. 4b, 4c and 4d are, respectively, the substrate construction, circuit symbol and I=V characteristics of a Shockley diode.

The pulse generators described herein use devices or circuits having the characteristics of Shockley diodes, and which are referred to herein as uncontrolled solid state devices (USDs) as defined above. Unlike SCRs and IGBTs, a Shockley Diode does not require a gate drive signal to initiate it from a high impedance state to a state of lower impedance. FIG. 4b shows the substrate construction of a Shockley diode as a four layer silicon device with respective doping densities P1, N1, P2 and N2.

Figure 4C:
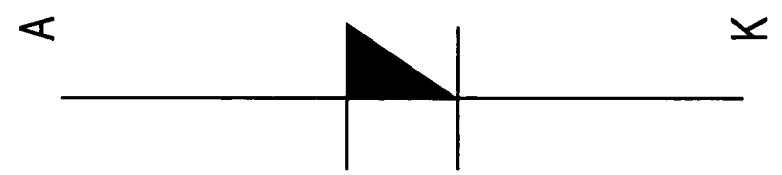
Figure 4B:
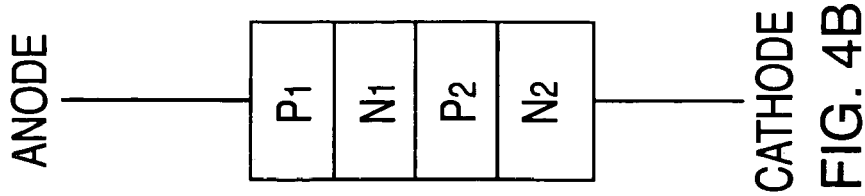

FIG. 4c shows the symbol used to denote a Shockley diode; note that there are only two connecting terminals. Essentially, a Shockley diode is unidirectional in that it can only change from its default high impedance state to a state of reduced impedance when the polarity of the applied signal is in a particular direction to forward bias the device, see FIG. 4d. Applying a signal of opposite polarity will fail to change the device's state unless the voltage exceeds its reverse breakdown voltage (Vr). A characteristic of a Shockley diode is that as a voltage is applied across the device in the forward bias direction, the device will only change to its lower impedance state if the voltage exceeds a predetermined threshold (Vth). Shockley diodes, however, are not readily commercially available and those that are typically only capable of withstanding small voltages and currents. However, this limitation can be overcome by arranging other commercially available devices to perform the equivalent function for high voltages and currents.

FIG. 4e is a high voltage, high current, implementation of a "breakover" USD, equivalent to a Shockley diode, using a DIAC and a TRIAC. Note that the overall circuit of FIG. 4e has only two terminals, an anode A' and a cathode K'. The TRIAC will change to a state of low impedance allowing a high current to flow when an appropriate voltage is applied to its gate terminal g. The combination of resistors R1 and R2 form a voltage divider, dividing the voltage V down to a voltage Vb, referenced to the cathode K', at the base of the transistor T1, where $Vb=V[R2/(R1+R2)]$. The emitter follower configuration of transistor T1 keeps the voltage applied to the DIAC at point X at approximately 0.7 Volts below the voltage Vb.

The DIAC will remain in its default high impedance state unless the voltage across it exceeds its threshold voltage Vd. Unless this voltage threshold is exceeded therefore, the USD will remain high impedance between A' and K'. If, however, the voltage at X exceeds the DIAC's threshold Vd, the DIAC will fold back and allow a voltage to appear at the gate of the TRIAC, and the TRIAC will then change to its low impedance state allowing a high current to flow between A' and K'. The overall voltage at which the USD changes state can therefore be accurately set by the voltage divider R1/R2. If the USD is desired to change to its low impedance state when the voltage V across it, i.e. across the terminals A' and K', reaches a certain threshold Vth, then the values of R1 and R2 are chosen such that this voltage Vth causes the voltage at X to be equal to the DIAC threshold voltage Vd; i.e. one solves the equation $Vd=[Vth(R2/(R1+R2))]-0.7$ for R1 and R2. Resistor R3 limits the current flow into the gate terminal of the TRIAC and prevents the gate from being damaged by the relatively high voltage across the terminals A' and K'. Note that with the state change of the device being determined by the ratio of R1 and R2, and the supply to the DIAC being performed by R3 through the current gain of T1, the values of both R1 and R2 can be kept high. Using high impedance values for R1 and R2 means that in the high impedance state there is very little current leakage through the USD. The diode D1 opposes any current flow in the reverse bias direction and in effect determines the reverse breakdown characteristics for the USD.

Note that any device which can be placed in a low impedance state from an initial state of high impedance could be used in place of the TRIAC in FIG. 4e, for example the USD could have employed a combination of IGBTs, SCRs, FETs (field effect transistors) or BJTs (bipolar junction transistor). The various implementations possible will be known to those skilled in the art.

Figure 4F:
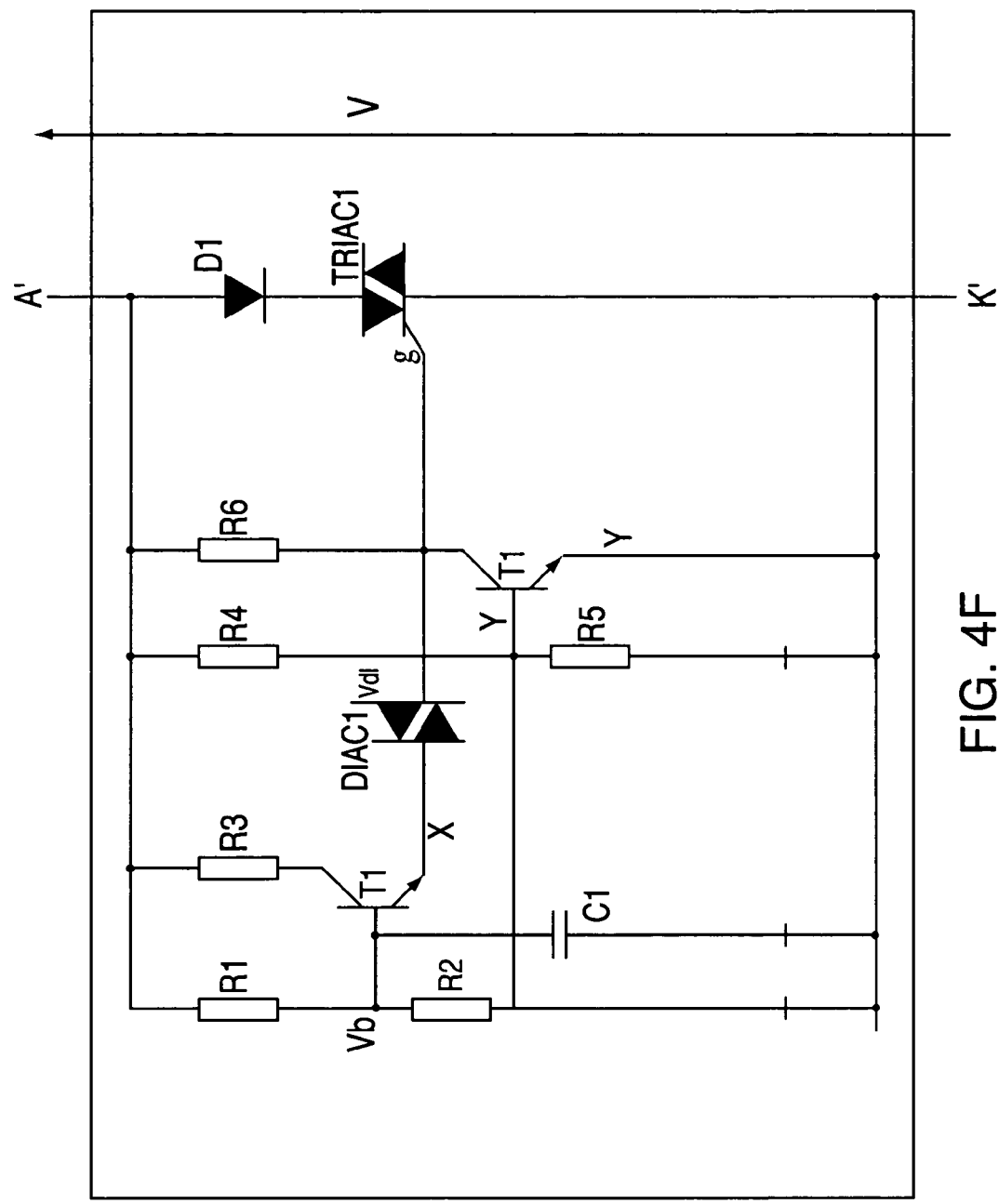

FIG. 4f shows another USD where the device has been configured to change to a state of low impedance if the instantaneous voltage across the anode A' and cathode K' exceeds a well defined threshold Vl, yet does not exceed an even higher voltage threshold Vh. In other words, if the voltage V applied across the device in FIG. 4f is within a well specified range from Vl to Vh the device will enter its low impedance state, while if it is outside this range, the device will remain in its default high impedance mode. With this particular characteristic the device is termed a "breakunder" USD. FIGS. 4g and 4h show the device's circuit symbol and I–V characteristics respectively.

The implementation of the breakunder USD in FIG. 4f is similar to that of the breakover device in FIG. 4e. The main difference is the presence of a capacitor C1 and a second transistor T2. Capacitor C1 limits the rate of change of voltage across R1. This in turn limits the rate of change of voltage across the DIAC. Since the voltage across the DIAC is slow to rise, if the voltage Y at the base of T2, as determined by the voltage divider R4/R5, rises above the forward bias voltage across T2's base emitter-junction before the DIAC voltage reaches its threshold Vd, the transistor T2 will turn on to short the gate of the TRIAC to K' and thus inhibit any current flow into the gate of the TRIAC. Using this arrangement, the upper voltage threshold Vh can be set by the voltage divider R4/R5 and the lower threshold Vl can be set as before by R1/R2.

Any breakunder device can further be arranged so that, once a voltage has been applied across its terminals large enough to exceed the upper threshold Vh so keeping the device in the high impedance state, if the applied voltage drops in magnitude the device will remain in the high impedance state. In this mode, in order to change to the low impedance state, the current must be reduced to almost zero and then re-applied. This later device is referred to as a breakunder USD with hysteresis.

Figure 5A:
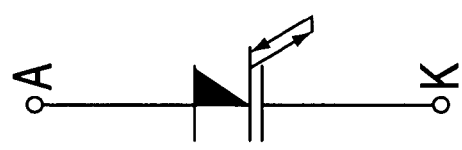
FIGS. 5a and 5b are, respectively, the circuit symbol and a circuit diagram for a breakunder USD with hysteresis.
Figure 5B:
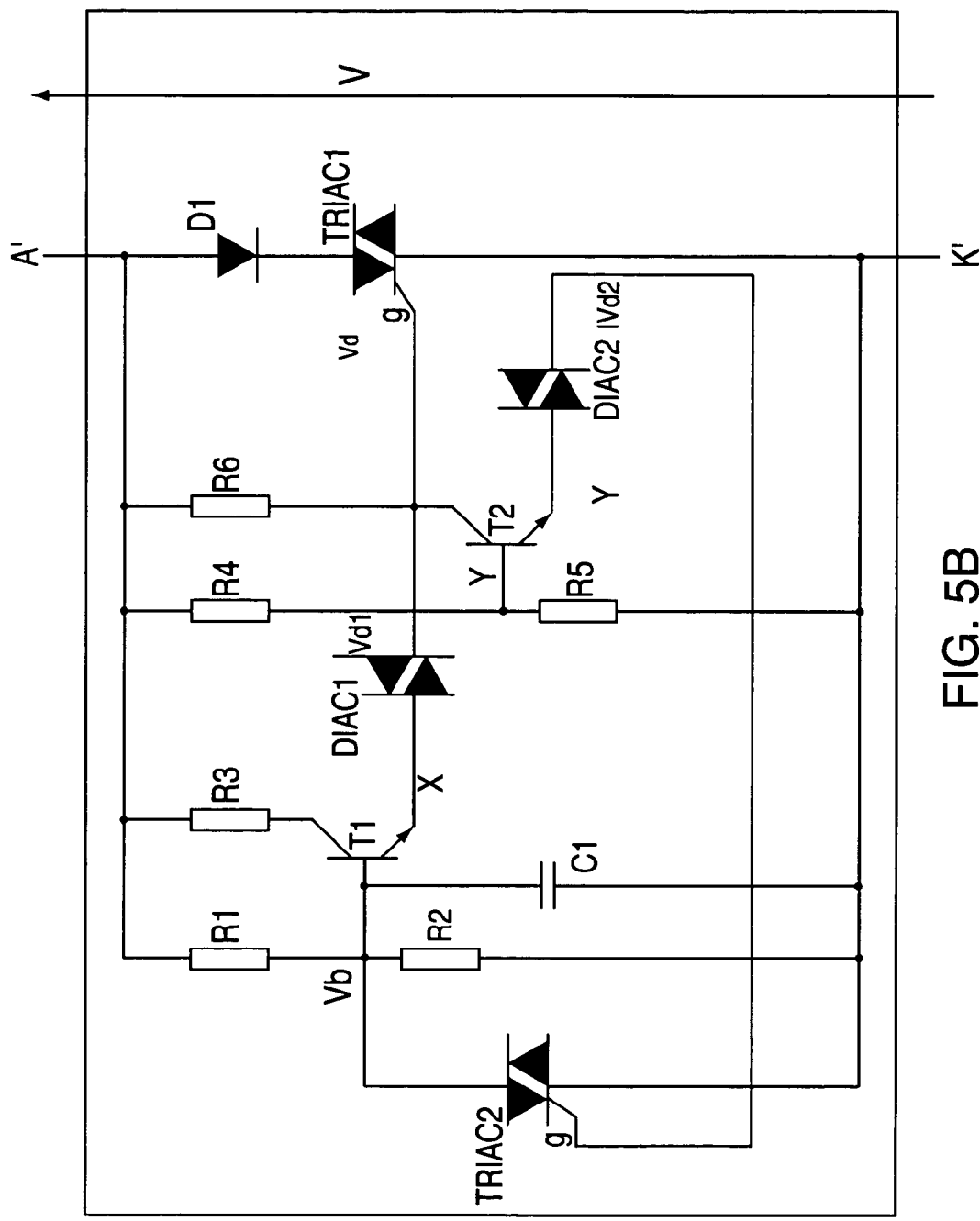

FIG. 5a shows the circuit symbol for a breakunder USD with hysteresis. FIG. 5b shows an implementation of the device based upon the breakunder device shown in FIGS. 4f–h. Only the differences will be described. A transistor T2 now forms a second emitter follower supplying a second DIAC, DIAC2. The voltage at point Y is designed to have a value equal to the threshold of DIAC2 when the voltage V across A', K' is equal to an upper threshold Vh. From FIG. 5b it can be seen that, unlike the voltage at point X, the voltage at point Y will instantaneously follow V and will be a proportion of V according to the ratio set by R4 and R5. If the voltage V causes the voltage at Y to exceed the voltage threshold of DIAC2, then a second TRIAC, TRIAC2, will enter a low impedance state. As soon as TRIAC2 enters its low impedance state, the voltage Vb at the base of T1 will reduce to almost zero. Once TRIAC2 has entered a low impedance state T1 cannot supply any current to DIAC1 and therefore the gate of TRIAC1. This "feedback" enhancement of FIG. 4 has introduced a level of hysteresis in to the arrangement. The only way now for TRIAC1 to enter its low impedance state is for the voltage across A', K' to be reduced to zero and then a new voltage applied which has a value between the lower threshold set by R1, R2 and DIAC1 and the upper threshold set by R4, R5 and DIAC2. This device has essentially three modes, two high impedance and one low impedance. If the instantaneous voltage applied to the arrangement is below the lower threshold Vl, then the combination of R1, R2 and T1 means that DIAC1 does not pass current and TRIAC1 remains in it's high impedance state. If the applied voltage is greater than the lower threshold Vl and less than the upper threshold Vh, then the combination of R4, R5 and T2 means that DIAC2 does not pass current and with DIAC1 now passing current, once the voltage across C1 has had sufficient time to rise, to the gate of TRIAC1, TRIAC1 enters its low impedance state. If, however, the applied voltage is greater than the upper threshold Vh, then the combination of R4, R5 and T2 means that DIAC2 does pass current to the gate of TRIAC2 thereby inhibiting DIAC1 and keeping TRIAC1 in its high impedance state.

It should be noted that any of the USDs of FIGS. 4e to 5 could be implemented as doped silicon layers in a single discrete integrated device. None of the devices require any external control and have the characteristic that they will conduct if the voltage across their two terminals A' and K' is either above and/or below a specified threshold. Another characteristic is that once in their low impedance state, they can only be returned to their high impedance state if the current flow through them is reduced to near zero. At exactly which current they will drop-out is dependent upon the particular device used.

Figure 6:
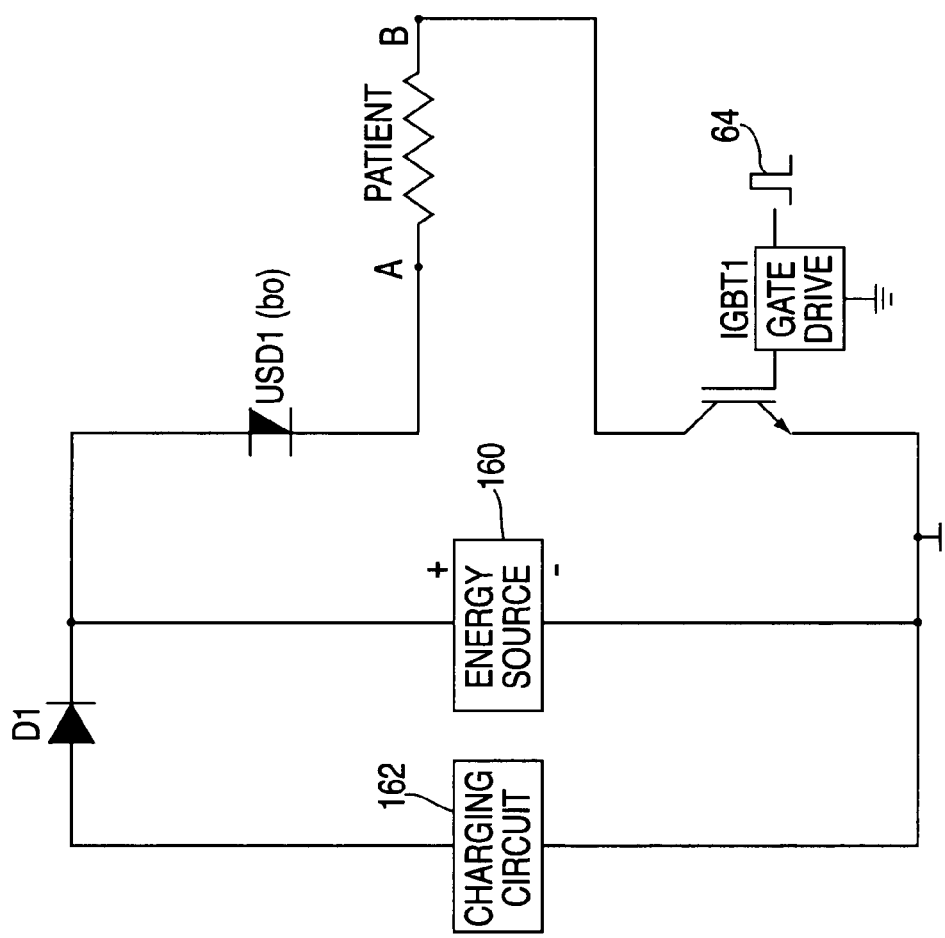
FIG. 6 is a circuit diagram of a defibrillator using a first implementation for the pulse generator.

FIG. 6 shows a basic implementation of a defibrillator, designed to provide a monophasic output voltage pulse across a pair of patient electrodes A and B. The defibrillator has an energy source 160, in this instance a capacitor which is charged up by a charging circuit 162, and an output circuit for connecting the voltage on the capacitor across the electrodes A, B upon the occurrence of a control signal 164. The output circuit comprises a first current path connecting the +ve side of the energy source 160 to the electrode A and a second current path connecting the −ve side of the energy source to the electrode B. The first current path contains a breakover USD, USD1(bo), while the second current path contains an IGBT, IGBT1. The breakover USD1(bo) will allow the current from the energy source 160 to flow through the load (patient) connected across the output electrodes A and B if the voltage applied from the energy source is large enough to exceed its threshold. The breakover USD1(bo) can be constructed as described with reference to FIG. 4e.

Initially, both sides of the load see a high impedance into A and B. Applying a gate drive pulse 164 to IGBT1 turns the latter on and drops the entire energy source voltage across USD1(bo). Provided the energy source is charged to a voltage above the threshold for USD1(bo), the latter will change to its low impedance state. The energy source now begins to discharge into the load. Removing the drive pulse 164 from the gate of IGBT1 after a pre-determined time period causes IGBT1 to return to its high impedance state and the current in the circuit reduces to approximately zero. With almost zero current flow, the device USD1(bo) recovers and the load once again sees a high impedance on both sides of A and B.

The use of the USD between electrode A and the +ve terminal of the energy source means that there is no isolated controlling circuit connection required. The only controlling element in the circuit of FIG. 6 is the gate of IGBT1 and this is referenced to the circuit ground so no isolation barrier is needed. The conventional diode D1 is used to prevent current flow back into the charging circuitry when charging is complete. The output generated by the circuit of FIG. 6 is a simple monophasic truncated exponential waveform.

Although FIG. 6 shows only one USD in the first current path, it will be understood that the voltage that can be withstood by the output circuit in the high impedance state can be increased by totem-poling two or more USDs in the first current path, as described previously. Two or more USDs in series actually behave just like a single USD with a threshold Vth which is the sum of the thresholds of the individual devices.

Figure 7:
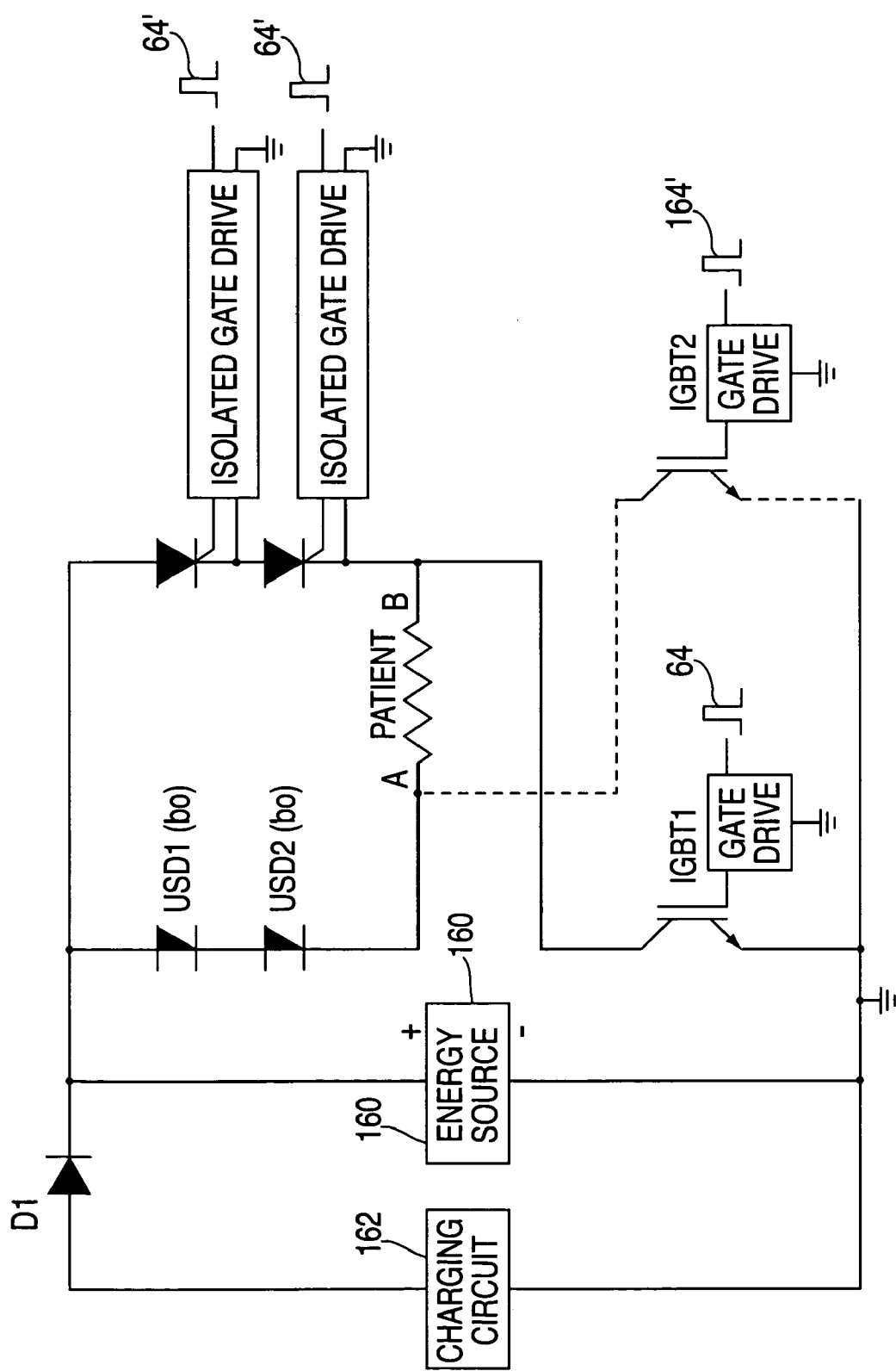
FIG. 7 is a circuit diagram of a of defibrillator using a second implementation of a pulse generator.

FIG. 7 shows an implementation of a defibrillator designed to provide a biphasic truncated exponential output voltage pulse across the patient electrodes A and B. Essentially, the implementation of FIG. 6 has been modified to add third and fourth current paths, shown by dashed lines. The third current path connects the +ve side of the energy source 160 to the electrode B and the fourth current path connects the −ve side of the energy source to the electrode A. The third current path contains two "totem-poled" SCRs, SCR1 and SCR2, while the fourth current path contains a further IGBT, IGBT2. The first and second current paths are as before, except that the first current path is shown with two totem-poled breakover USDs, USD1(bo) and USD2(bo). The USDs may be as shown in FIG. 3. For reasons previously described, the SCRs have isolated gate drives.

In operation, the energy source 160 is first charged to a voltage exceeding the threshold Vth of the totem-poled USDs. Then, at time t0 (see FIG. 8), the device IGBT1 is given a gate pulse 64 placing it into its low impedance state. This places substantially the entire voltage of the energy source across the totem-poled USDs (two USDs are used as previously stated to increase the voltage that the circuit can withstand). The USDs therefore turn on (the devices SCR1, SCR2 and IGBT2 remaining in their high impedance state), and a current flows through the load from electrode A to electrode B. As energy is removed from the energy source by the load, the voltage applied by the energy source decays. At a later time t1, the IGBT1 has its gate signal removed and it returns to its high impedance state. This causes the current in the circuit to reduce to almost zero so returning the devices USD1(bo) and USD2(bo) to their high impedance states. The instant t1 is chosen so that at that point the voltage remaining on the energy source is below the threshold Vth of the totem-poled devices USD1(bo) and USD2(bo).

Figure 8:
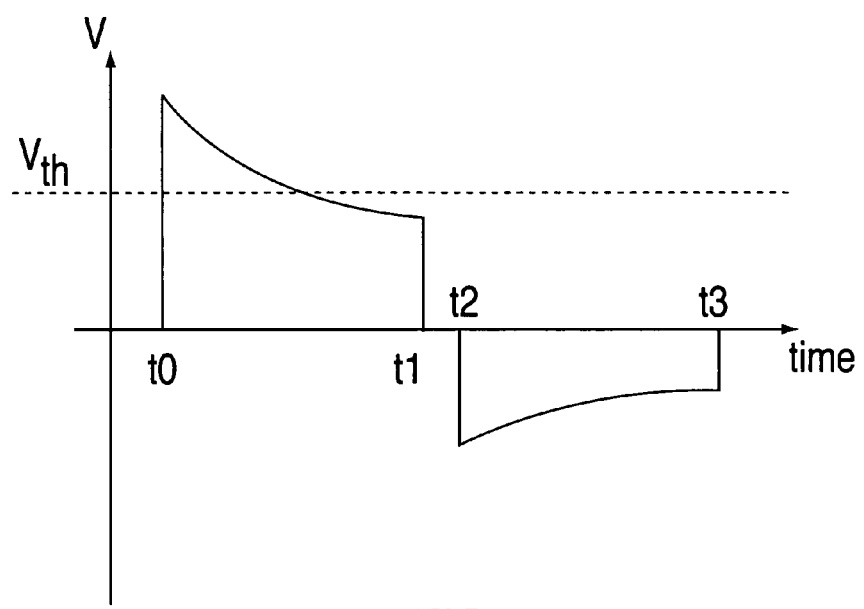
FIG. 8 is an example of the waveform that can be produced by the implementation of FIG. 7.

Now, at a time t2 following shortly after t1, the devices IGBT2, SCR1 and SCR2 are given simultaneous gate drive pulses 64' to place them in their low impedance state. Now a discharge current flows in the opposite direction through the load, i.e. from electrode B to electrode A. After a further pre-determined time period has elapsed the gate drive to device IGBT2 is removed at t3 and the current flowing in the circuit is reduced almost to zero. Again this causes the two SCRs to also return to their high impedance state. The resulting output is as shown in FIG. 8.

In this circuit isolated gate drives are required for the SCRs. However, only two such isolated gate drives are required in this case. The methods used by prior art would have required at least four isolated gate drive circuits. Also only four devices are required to be controlled in total instead of the six control lines previously necessary.

Figure 9:
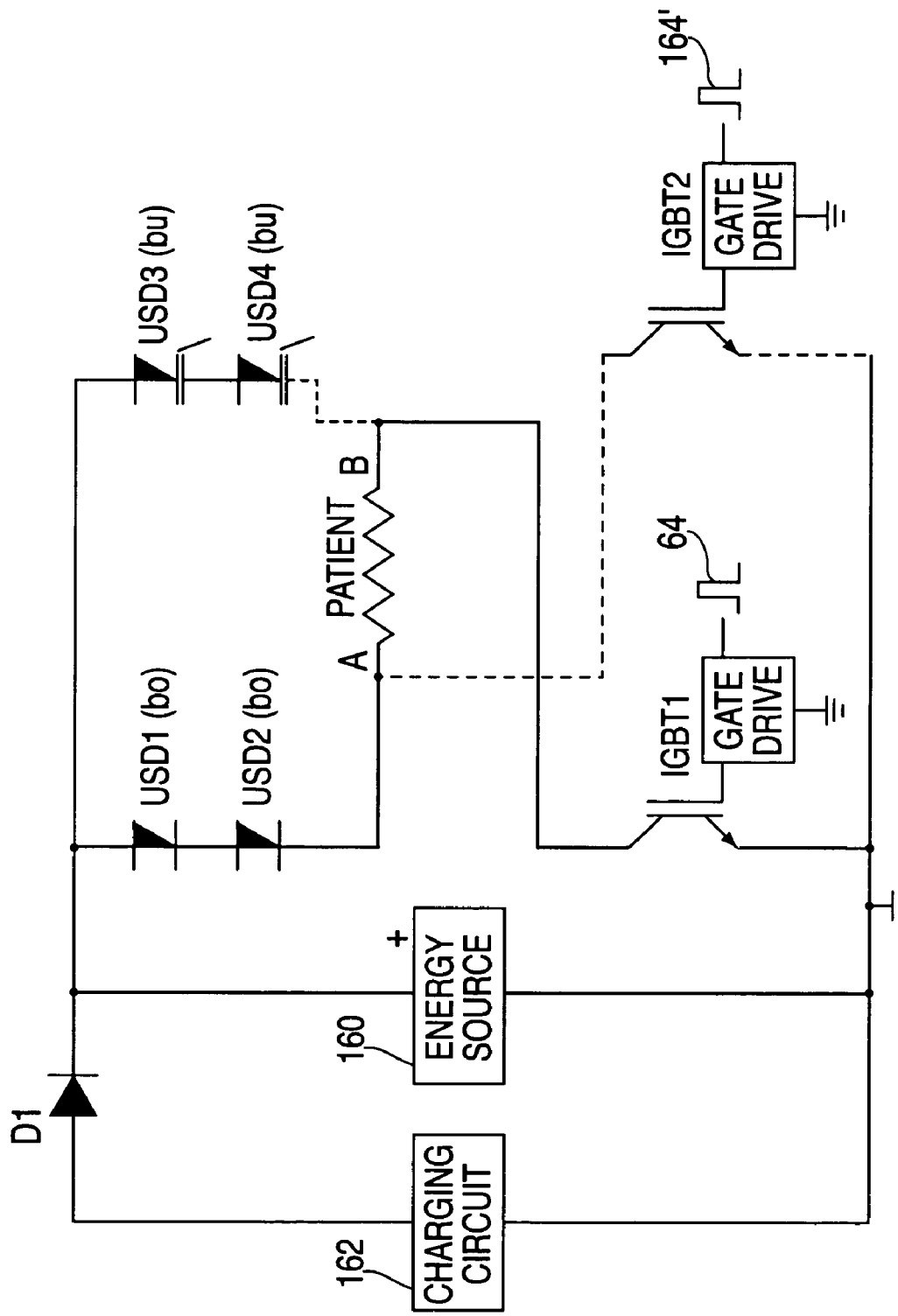
FIG. 9 is a circuit diagram of a defibrillator showing a third implementation of the pulse generator.

FIG. 9 shows a third implementation of the pulse generator. This differs from the implementation of FIG. 7 in that the totem-poled SCRs, SCR1 and SCR2, have been replaced by totem-poled breakunder USDs with hysteresis, USD3(bu) and USD4(bu).

In operation, the energy source 160 is first charged to a voltage greater than the threshold Vth of the totem-poled breakover USDs and also greater than the upper voltage threshold Vh of the totem-poled breakunder USDs. Then, at time t0 (see FIG. 8, which also apples in this case), the device IGBT1 is given a gate pulse 164 placing it into its low impedance state. This places substantially the entire voltage of the energy source across the totem-poled breakover USDs, USD1(bo) and USD2(bo). All other devices remain in their high impedance state (the breakunder USDs because the voltage is above their upper threshold Vh; this is important because otherwise they would turn on and bypass the load). The breakover USDs therefore turn on and a current flows through the load from electrode A to electrode B. As energy is removed from the energy source by the load, the voltage applied by the energy source decays. At a later time t1, the IGBT1 has its gate signal removed and it returns to its high impedance state. This causes the current in the circuit to reduce to almost zero so returning the devices USD1(bo) and USD2(bo) to their high impedance states. The instant t1 is chosen so that at that point the voltage remaining on the energy source is below the threshold Vth of the totem-poled devices USD1(bo) and USD2(bo) but between the upper and lower voltage thresholds Vl, Vh of the totem-poled devices USD3(bu) and USD4(bu).

Now, at a time t2 following shortly after t1, the device IGBT2 is given a gate drive pulse 64' to place it in its low impedance state. Now the devices USD3(bu) and USD4(bu) turn on, because the voltage applied across them is between their upper and lower voltage thresholds, and a discharge current flows in the opposite direction through the load, i.e. from electrode B to electrode A. After a further pre-determined time period has elapsed the gate drive to device IGBT2 is removed at t3 and the current flowing in the circuit is reduced almost to zero. Again this causes USD3(bu) and USD4(bu) to return to their high impedance state. The resulting output is as shown in FIG. 8.

Of particular note is that for this arrangement there are no isolated connection gate control connections to any of the devices in the circuit. Also only two devices (IGBT1 and IGBT2) require control signals and these are both direct electrical connections referenced to circuit ground. This is a significant saving in size and component cost. Furthermore, to control the entire circuit only requires two control signals rather than the five that would be otherwise be necessary. The control circuit can now simply pulse one IGBT, IGBT1, to produce the first phase of the output waveform and pulse the second IGBT, IGBT2, to produce the second phase of the output.

Figure 10:
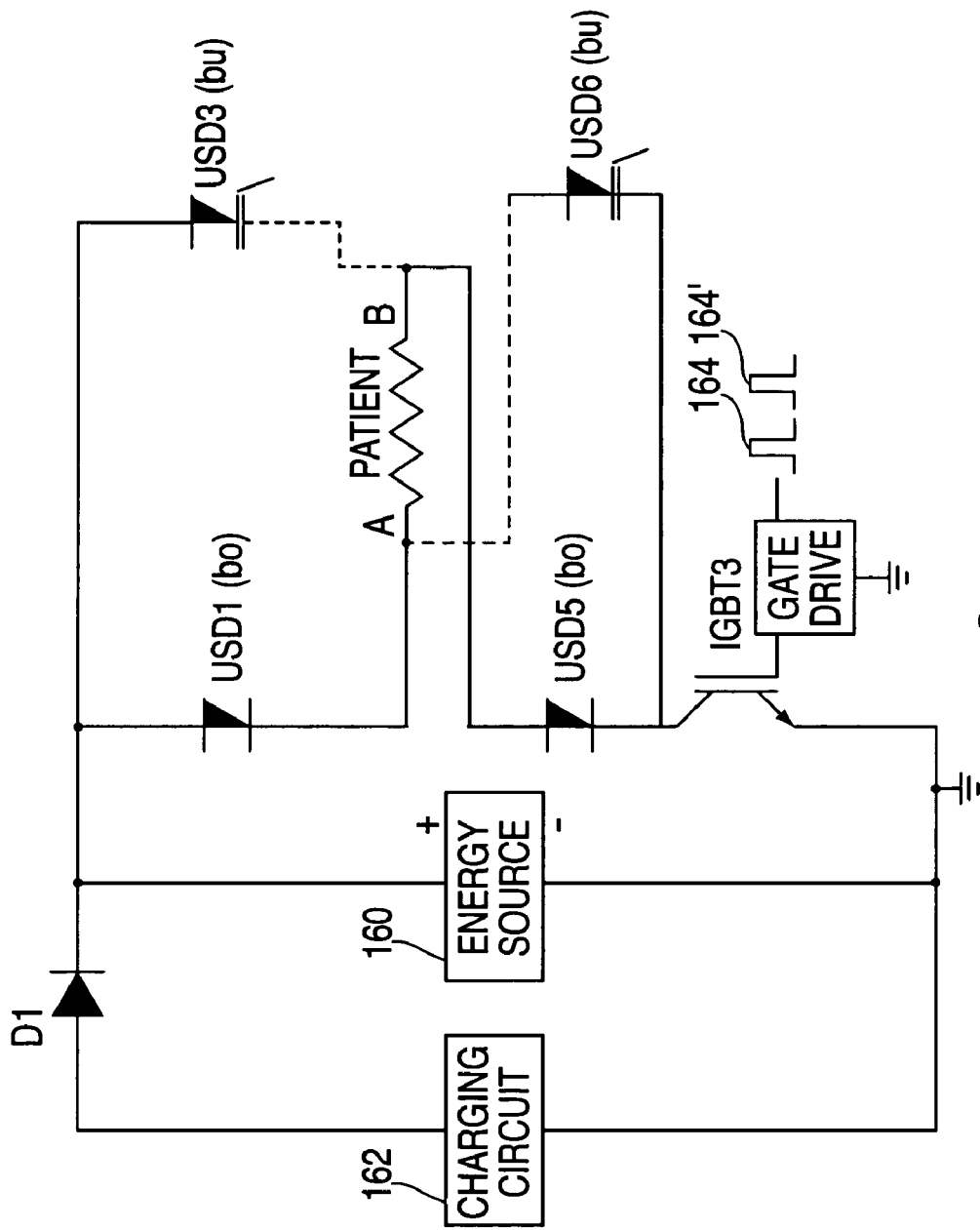
FIG. 10 is a circuit diagram of a fourth implementation of the pulse generator.

FIG. 10 shows a fourth implementation of the pulse generator. This differs from the implementation of FIG. 9 in that the two IGBTs, IGBT1 and IGBT2, have been replaced by a breakover USD, USD5(bo), and a breakunder USD, USD6(bu), respectively. Also, an IGBT (IGBT3) has been added in common to the second and fourth current paths. For simplicity the circuit uses single USDs (USD1(bo) and USD3(bu) respectively) in the first and third current paths, although as described two or more such devices can be totem-poled in each path to increase the ability of the circuit to withstand higher voltages. Although this arrangement has added another circuit element, IGBT3, the output circuit is fully automatic and all devices connected to the load across A and B are uncontrolled. The only controlling signal required is the signal to the gate of IGBT3 in the common ground return.

In operation, having charged the energy storage device 160 to a voltage greater in magnitude than the threshold of breakover devices USD1(bo) and USD5(bo), and also high enough not to enter the threshold range which would place USD3(bu) and USD6(bu) into their low impedance state, a gate drive pulse 64 applied to IGBT3 will turn on USD1(bo) and USD5(bo) and cause current to follow through the load in the direction from A to B. Removing the gate drive to IGBT3 after a pre-determined time interval will, as before, reduce the current in the circuit to almost zero and all devices will return to their high impedance states. Provided the voltage across the energy storage device is now less than the threshold for USD1(bo) and USD5(bo), and furthermore providing the voltage is within the threshold required to allow the break-under devices USD3(bu) and USD6(bu) to enter their low impedance states, the application of a second gate pulse 164 to IGBT3 will cause the current to flow through the load in the opposite direction from B to A. Again, this causes the biphasic waveform of FIG. 8 to be generated.

Note that not only is there no requirement for any isolated connections to any of the devices but only one single device needs to have a gate drive signal applied in order for the whole circuit to be fully operated. It will be appreciated that this arrangement means that the whole output circuit including USD1(bo), USD5(bo), USD3(bu), USD6(bu) and IGBT3 could be easily implemented as a single integrated solid state component. This would further mean that the entire output stage would be a single encapsulated integrated module only requiring 5 connections. These connections would be a common ground connection, an input from an energy source, two output connections to the electrodes A and B and a single input control connection referenced to the common ground which would control the module. FIG. 11 shows the block diagram of a circuit including such an integrated circuit 66—note that even the gate drive circuit for the IGBT can be included in the module, leaving the control terminal into the circuit requiring a standard TTL type signal. This represents an enormous saving in terms of cost, size and complexity.

Figure 12A:
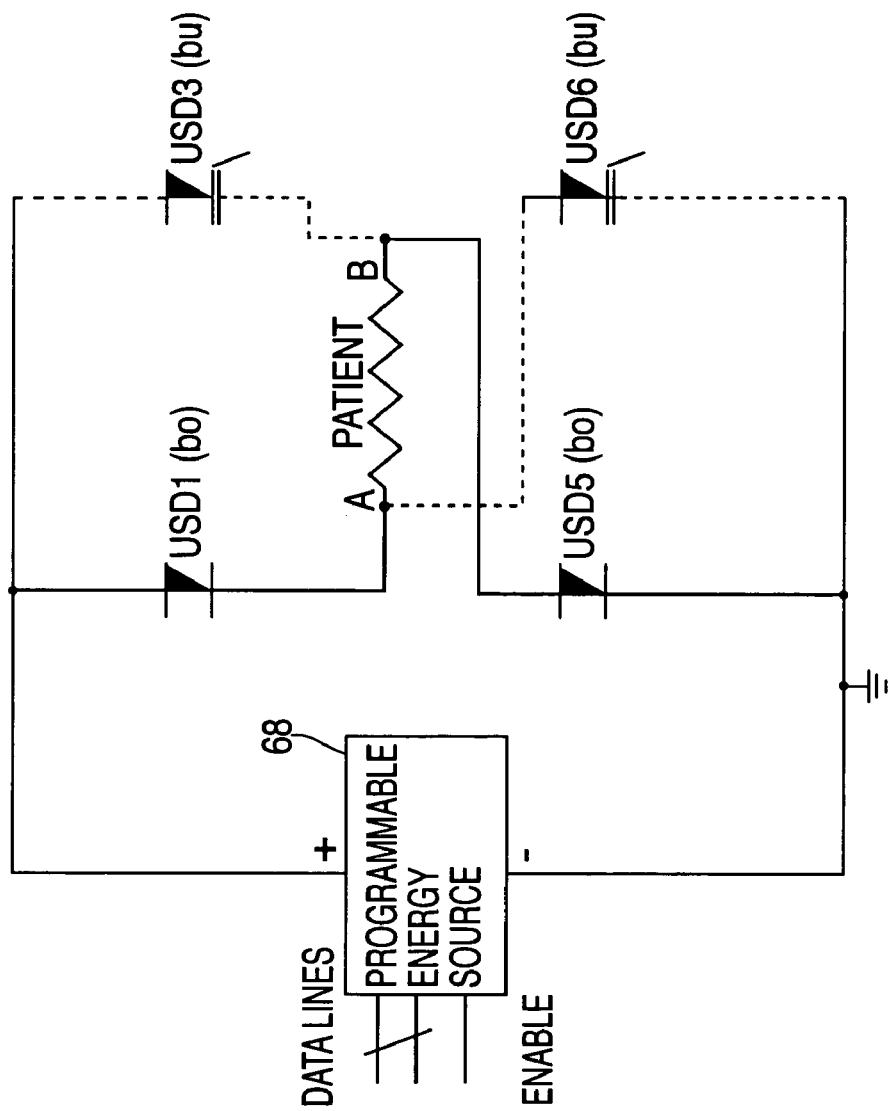
FIG. 12a is a circuit diagram of a fifth implementation of the pulse generator.
Figure 12B:
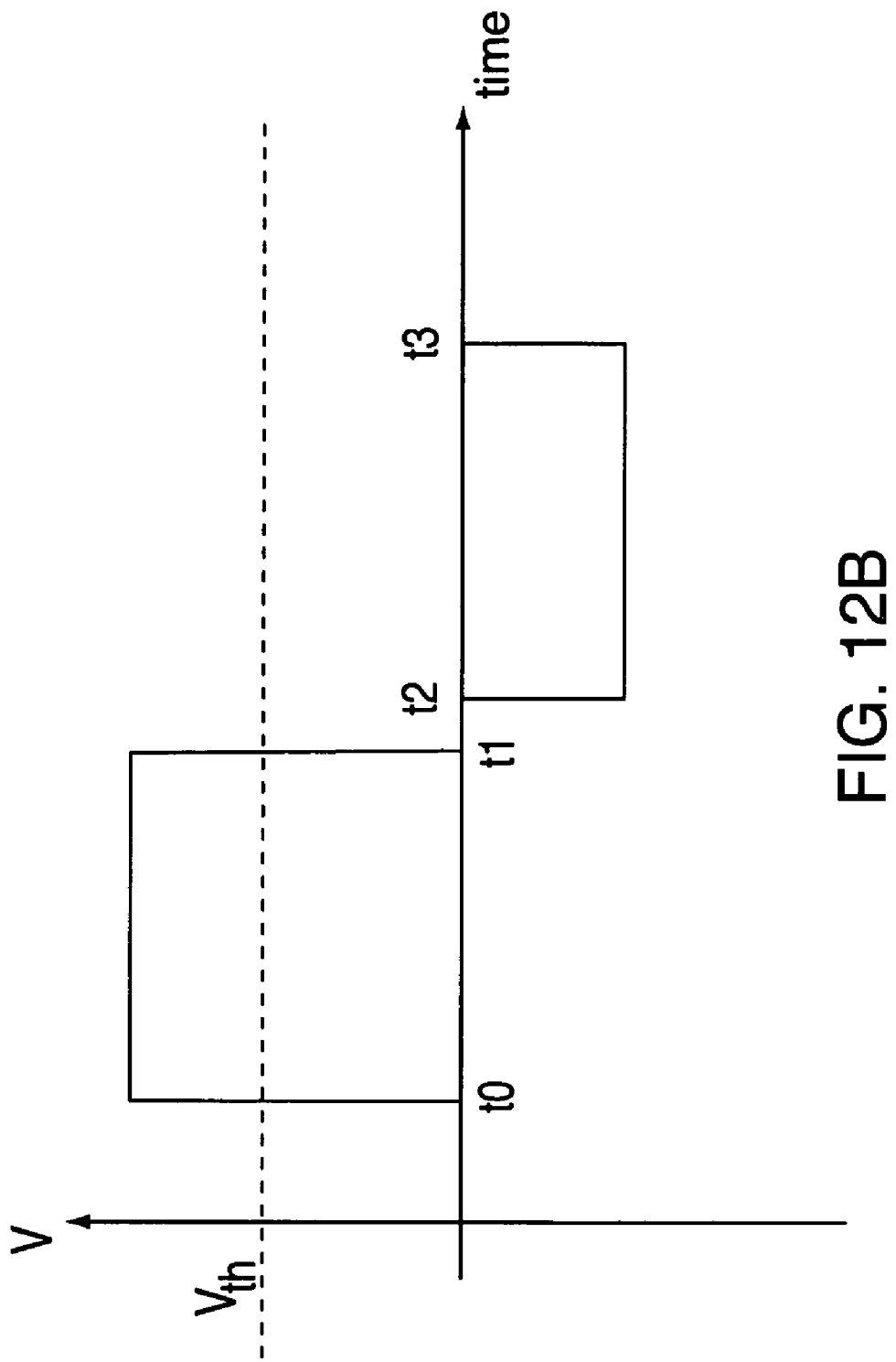

In a fifth implementation of the pulse generator, which is a modification of that shown in FIG. 10, and may likewise be formed with the output circuit as a single integrated circuit component, the energy source is a programmable active power supply 168, rather than a passive capacitor. Referring to FIG. 12a, here the energy source is designed to supply a programmed constant DC voltage, and with this voltage set at a level above the conducting threshold Vth of breakover devices USD 1(bo) and USD5(bo) and greater than the low impedance threshold range of break-under devices USD3(bu) and USD6(bu), the current again flows through the load from A to B. Setting the programmable power supply then to supply a voltage of zero volts for a pre-determined time interval causes all the devices to return to their high impedance state. Further setting it to supply a voltage which is less than the thresholds for USD1(bo) and USD5(bo), and within the threshold range required to allow the breakunder devices USD3(bu) and USD6(bu) to enter their low impedance state, will cause the current to flow in the opposite direction from B to A. The resulting waveform can be seen by way of example in FIG. 12b. It would also be possible to have several energy sources selectable by placing additional USDs within the circuit arrangement. Which energy source is to be used to supply the output circuit could then be selected at whatever times are desirable to achieve the pulse shape required.

It should be appreciated that further current paths containing USDs or other solid state devices could be added between the energy source and the electrodes A and B in any of the circuits described above, thereby allowing a third, fourth or subsequent phase to be added in a pre-determined polarity.

It should also be appreciated that further protective components may be necessary for reliable operation of the circuits in practice. By way of example, an inductor could be placed in series with the output of the energy source to limit the rate of change of current in the circuit. Such additions are well known to those skilled in the art.

In FIGS. 1–3 the cable 36 terminating in connector 48 may have several wires. In FIG. 3 three such wires are shown, 48A, 48B and 48C. Wires 48A and 48B provide a dual purpose. They are used to sense intrinsic cardiac activity, i.e., an ECG. Sensed signals are sent to the custom IC 70 which performs signal processing on these signals and then sends them to the microprocessor 66. The microprocessor uses the ECG to determine the current condition of the patient.

The second function of the wires 48A, 48B is to provide defibrillator pulses from the pulse generator 80.

An impedance detection circuit 82 may also be provided. This circuit may be connected across the wires 48A, 48B and used to detect the impedance of pads (not shown) used to apply the defibrillator pulses. This impedance is provided to the custom IC 70 and may be used to confirm that the wires 48A, 48B are not open and that the pads are attached to the patient properly.

Preferably the cable 36 and its terminating block 34A which are uniquely identified by an ID code stored in a memory 84. The terminating block 34 is connected to the electrodes or pads attached to the patient (not shown). The code stored in memory 84 can be obtained by the custom IC 70 using the third wire 48C. This code is checked before any pulses are applied to insure that the proper cable is used with the ADM 32.

The ADM 32 is operated as follows. First, it is attached mechanically and electrically to monitor 12 so that the two can form a single, integrated, composite system 10. The mechanical connection is not described here since it can be implemented using brackets or other coupling elements well known in the art. The electrical connections include the cable 40 for the power supply (if used) and a serial cable 38.

Once the ADM 32 is mounted, it can be configured, for the patient. For this purpose, the clinician operates the keys on face 52 to enter into a configuration mode or via the patient monitor. In this mode the clinician can select the parameters associated with the defibrillator therapy to be administered to the patient. The clinician can also set whether the ADM 32 operates in a fully automatic mode, an advisory mode, a manual mode, or a pacer mode. Typically, in an automatic mode the ADM 32 monitors the status of the patient and if fibrillation is detected then pulses from the biphasic pulse generator are delivered to the patient automatically. In the advisory mode, the ADM32 monitors the patient and generates audio and/or visual indication of the patient's status, including an indication of a fibrillation episode, makes the device ready to deliver defibrillation pulses, however, defibrillation pulses are not applied unless they are delivered by the clinician. In the manual mode the operation of the ADM 32 is under the complete control of the clinician. In the pacer mode, the clinician selects the pacing protocol and delivers the pacing pulses to the patient. The clinician enters the parameters required for all these operations via the knob 56 and switches 58 in response to prompts shown in the display 54. In the Figures, the same wires are shown for both sensing the intrinsic cardiac activity of the patient and delivering the high voltage biphasic defibrillator pulses. Of course, separate wires, terminating in appropriate electrodes and/or pads may be used as well. In this manner, the ADM 32 can deliver defibrillation (or other kinds of), therapy to a patient using any of the protocols well known in the art. An external defibrillator describing some protocols that may be used is described in commonly owned co-pending application Ser. No. 09/452,507 filed Dec. 1, 1999 entitled AUTOMATIC EXTERNAL CARDIOVERTER/DEFIBRILLATOR WITH TACHYARRHYTHMIA DETECTOR USING A MODULATION (AMPLITUDE AND FREQUENCY) DOMAIN FUNCTION, now U.S. Pat. No. 6,289,243 incorporated herein by reference. Of course other protocols and modes of operation may be used as well.

Importantly, during its operation, ADM 32 continuously exchanges data with the monitor 12 over the serial cable 38. For example, the ADM 32 needs to generate a digital representation of the ECG for its determination of the patient's status. This digital ECG is transmitted to the monitor for its display 18. Under the direction of the microprocessor 66, the ADM 32 may send various other information to the monitor 12, including, for example, its current mode of operation (manual, advisory, automatic). The ADM 32 may also send data descriptive of various stages of its operation, including data indicative of the status of the patient, the voltage on the capacitors of the biphasic pulse generator, time required to charge the capacitors to a nominal voltage, time until the next pulse is applied, time expired since the last pulse, number of pulses applied to the patient, readiness of the ADM to apply a pulse, etc. The ADM 32 may also include a self-testing feature. The results of this self test may also be sent to the monitor. The information sent to the monitor 10 may be shown immediately on display 18, may be sent to the printer 28 for a hard copy and may also be stored in the memory of the monitor (not shown). In addition, the data from the ADM 32 may be transmitted to other sites if the monitor is connected to a network.

The monitor 10 may also send data to the ADM 32, including acknowledgments of the data received. Typically monitor 12 may be capable of monitoring one or more physiological functions of the patient such as blood pressure, arterial pulse oximetry $(SpO)_2$, carbon dioxide $(CO_2)$, respiration, and cardiac output. Some monitors may be capable of generating a digital ECG signal. While it is expected that the ECG signal detected by the ADM 32 through its electrodes may be more reliable, the external ECG signal from the monitor may be used as a backup in case the ECG signal cannot be detected locally, or as a means of confirming the validity of the local ECG signal by the ADM. Moreover, the ADM 32 may be adapted to determine the condition of the patient and other information based on other physiological parameters of the patient as well. For example, the ADM 32 may use any of the physiological parameters derived by the monitor 12 to determine whether the patient has a cardiac condition which needs therapy to be delivered by the ADM 32. These other physiological parameters may be provided to the ADM 32 by the monitor 12 as well.

In addition, the memory 68 may be insufficient for data logging purposes. Therefore the ADM 32 may send some data for storage in memory 30 of monitor 12. The monitor 12 can then return this data to the ADM 32 as requested.

As described above, the ADM 32 is adapted to perform a self-test and to monitor the status of the patient. If the self-test indicates that the ADM 32 may be malfunctioning, or if a patient condition is detected which should be brought to the attention of the clinician, the ADM 32 is adapted to generate an alarm signal. This alarm signal may be used to activate the audible and visual signals on the ADM 32 and/or the monitor 12. In addition, these signals may be transmitted to a remote location via the communications network connected to interface 22. The communications network may be a wired or wireless network. Therefore the term 'network' is used herein very broadly to cover any analog or digital communications network capable of transmitting information from the system 10 to another location, including local area networks, wide area networks, Internet connections, paging cellular telephones, telemetry, and satellite communications, just to name a few.

Some monitors presently available are designed so that they can be interfaced with other apparatus, like the ADM 12 using a standard protocol such as Spacelabs Universal Flexport Protocol. If no such protocol is available for a particular monitor, the ADM 32 can be programmed so that it can communicate with monitor 12 using the unique protocol characteristic of the monitor 12.

In summary, an automatic defibrillator module is described which can be integrated with a patient monitoring device such that the two can share various functions. More specifically, the ADM 32 includes the components necessary to analyze the condition of the patient and to generate, if necessary, therapeutic pulses. Data from the ADM 32, including a digital ECG and other signals indicative of the operation of the ADM 32 are sent to the monitor 12 for display, printing, and/or storage. Thus, the ADM 32 may or may not have its own ECG display, a printer or data logging memory. It is expected that the overall combination of a monitor and ADM requires less space, is cost-effective and very flexible since the same ADM can be used with many different patient monitors from different manufacturers.

In the embodiment described above, programming information for the ADM 32 is entered using the controls on the face of the ADM while patient specific information is displayed or otherwise provided on the monitor 12. Of course other arrangements may be made as well. For example, the programming information may be entered from the monitor 12 and/or some of the patient specific information can be displayed by the ADM 32. Moreover, the ADM 32 may also incorporate a printer which may be dedicated for information from the ADM 32 or may be shared by the monitor 12. Moreover, the ADM 32 may also be arranged to sense other physiological parameters besides ECG as well and to transmit the same to the monitor 12.

Obviously, numerous modifications may be made to this invention without departing from its scope as defined in the appended claims.

We claim:

1. A composite monitoring system comprising:
   a patient monitor including a sensor arranged to sense a physiological characteristic of a patient and a signal processor coupled to said sensor and adapted to process the signal from said sensor, said patient monitor having one of several operational sets of operational characteristics and generating an output indicative of said physiological characteristics; and
   a defibrillator module adapted to be selectively coupled to said patient monitor, said defibrillator module including a pulse generator responsive to commands to generate therapeutic pulses for the patient, and a data generator arranged to generate indication signals indicative of an operation of said defibrillator module, said defibrillator module being programmable to interface with several patient monitors having different sets of operational characteristics, said patient monitor being programmed to interface said patient monitor based on said one set of operational characteristics.

2. The system of claim 1 wherein said output member includes a display generating visual images.

3. The system of claim 1 wherein said output is fed to a printer adapted to print a hard copy of said output.

4. The system of claim 1 wherein said sensor comprises a cardiac sensor adapted to generate an external ECG and wherein said patient monitor is adapted to transmit said external ECG to said defibrillator module.

5. The system of claim 1 wherein said sensor is adapted to sense at least one of the physiological parameters selected from the group consisting of blood pressure, arterial pulse oximetry $(SPO)_2$, carbon dioxide $(CO_2)$, respiration, and cardiac output.

6. The system of claim 1 wherein said defibrillator module includes a defibrillator display.

7. The system of claim 6 wherein said defibrillator module includes a defibrillator display arranged to provide information associated with the selection of said operational parameters.

8. The system of claim 1 wherein said defibrillator module includes a selector arranged and constructed to allow an operator to generate operational parameters for said defibrillator module, said operational parameters defining a mode of operation for said defibrillator module.

9. The composite system of claim 1 wherein said defibrillator module is adapted to operate in one of an automatic, semiautomatic and manual modes.

10. A composite monitor/defibrillator unit comprising:
    a first external patient monitor having one of several operational characteristic sets;
    a physiological sensor to sense the intrinsic cardiac activity of a patient and to generate a sensor signal indicative of said intrinsic cardiac activity;
    a controller arranged to receive said sensor signal and to generate corresponding commands;
    a pulse generator arranged to generate therapeutic pulses for the patient in response to said commands;
    an output member associated with said controller and adapted to generate output signals indicative of an operation of the defibrillator, said output signals being selected for transmittal to said external patient monitor for display;
    programming means for programming said output member to generate said output signals to match the operational characteristics of several patient monitors with different operational characteristics, said programming means being set to function with said first patient monitor;
    wherein said physiological sensor, controller, pulse generator and output member are coupled electrically and mechanically to said external patient monitor to form an integral system.

11. The module of claim 10 wherein controller includes an arrhythmia detector arranged to receive said sensor signal and to determine a cardiac condition of the patient that requires therapy.

12. The module of claim 11 wherein said output member is adapted to receive a physiological parameter detected by said external patient monitor, and wherein said arrhythmia detector is adapted to receive said physiological parameter and to make a determination for delivering therapy to the patient based on said physiological parameter.

13. The module of claim 10 wherein said output member is coupled to said pulse generator and is adapted to generate said output signals to indicate generation of pulses by said pulse generator for said patient monitor.

14. The module of claim 10 wherein said controller is arranged to define a plurality of modes of operation including a fully automatic, an advisory, a manual, and a pacing modes.

15. The module of claim 10 further comprising an alarm circuit arranged to generate an alarm signal indicative of one of a patient condition and a module condition.

16. The module of claim 15 wherein said module is adapted to send send alarm signal to a remote location over a communications network selected from a group consisting of hard-wired network, a wireless network, a local area network, a wide area network, the Internet, a paging system, a cellular telephone system, a telemetry system and a satellite system.

17. The module of claim 10 further comprising a display adapted to display said sensor signal.

18. A composite defibrillator assembly comprising:
a patient monitor adapted to sense and display a physiological parameter, said patient monitor having a specific set of operational characteristics; and
a defibrillator module arranged to be mechanically and electrically couple with said patient monitor to form an integrated composite system and including:
a controller arranged to receive a sensor signal indicative of the intrinsic cardiac activity of a patient and to generate corresponding commands, said controller being arranged to function with one of several patient monitors, said controller being set to match the specific operational characteristics of said patient monitor;
a pulse generator arranged to generate therapeutic pulses for the patient in response to said commands;
an output member associated with said controller and adapted to generate output signals indicative of an operation of the defibrillator, said output signals being selected for transmittal to said patient monitor for display;
wherein said patient monitor is operational without said defibrillator module.

19. The module of claim 18 further comprising a sensor adapted to sense said sensor signal.

20. The module of claim 18 wherein said controller is adapted for receive said sensor signal from said external patient monitor.

21. The module of claim 18 further comprising a physiological parameter detector that detects a physiological parameter, said controller being adapted to transmit said physiological parameter to said external patient monitor for display and processing.

* * * * *